United States Patent [19]

De Vroom

[11] Patent Number: 6,060,268
[45] Date of Patent: May 9, 2000

[54] PENICILLIN G ACYLASE IMMOBILIZED WITH A CROSSLINKED MIXTURE OF GELLED GELATIN AND AMINO POLYMER

[75] Inventor: Erik De Vroom, Leiden, Netherlands

[73] Assignee: Gist-Brocades B.V., Netherlands

[21] Appl. No.: 08/983,370

[22] PCT Filed: Jul. 16, 1996

[86] PCT No.: PCT/EP96/03253

§ 371 Date: Jan. 15, 1998

§ 102(e) Date: Jan. 15, 1998

[87] PCT Pub. No.: WO97/04086

PCT Pub. Date: Feb. 6, 1997

[30] Foreign Application Priority Data

Jul. 18, 1995 [EP] European Pat. Off. .............. 95201979

[51] Int. Cl.⁷ .............................. C12P 37/04; C12P 35/04; C12N 11/02; C12N 11/10
[52] U.S. Cl. .............................. 435/45; 435/50; 435/177; 435/178; 435/180
[58] Field of Search ............................... 435/174, 177, 435/178, 180, 182, 43, 44, 45, 46, 47, 48, 49, 50, 51

[56] References Cited

FOREIGN PATENT DOCUMENTS

| | | |
|---|---|---|
| 0122681 | 10/1984 | European Pat. Off. . |
| 0222462 | 5/1987 | European Pat. Off. . |
| 0297912 | 1/1989 | European Pat. Off. . |
| 473008 | 3/1992 | European Pat. Off. . |
| 2149816 | 6/1985 | United Kingdom . |
| 08287 | 6/1991 | WIPO . |
| 12782 | 8/1992 | WIPO . |
| 12250 | 6/1993 | WIPO . |

*Primary Examiner*—David M. Naff
*Attorney, Agent, or Firm*—Bierman, Muserlian and Lucas

[57] ABSTRACT

Penicillin G acylase is immobilized by covalent bonding to a crosslinked mixture of a gelled gelling agent such as gelatin and a polymer containing free amino groups such as alginate amine, chitosan or polyethylene imine. The immobilized penicillin G acylase provides a higher synthesis/hydrolysis ratio as compared to immobilizing with other carriers when producing β-lactam derivatives by a condensing reaction of an amino β-lactam with an acylating agent. The acylating agent may be a derivative of D-phenylglycine, a derivative of D-p-hydroxyphenylglycine or a derivative of D-2,5-dihydro-phenylglycine. Examples of β-lactam derivatives that can be produced are amoxycillin, ampicillin, cephaclor, cephadroxil, cephprozil, cephalexin and cephradine.

8 Claims, No Drawings

PENICILLIN G ACYLASE IMMOBILIZED WITH A CROSSLINKED MIXTURE OF GELLED GELATIN AND AMINO POLYMER

TECHNICAL FIELD

The present invention relates to an improved immobilized Penicillin G acylase. Furthermore, the invention relates to the preparation of β-lactam-antibiotics by enzymatic acylation of the parent amino β-lactam nucleus with the corresponding acylating agent using said immobilized enzyme.

BACKGROUND AND FIELD OF THE INVENTION

Enzymatic production of semisynthetic β-lactam antibiotics by acylation of the parent amino β-lactam moiety with an activated side chain acid derivative, such as an amide or an ester, is known from Dutch patent 158847, European patent applications 339751 and 473008, international patent applications WO 92/01061 and WO 93/12250, U.S. Pat. No. 3,816,253, and West German patent documents 2163792 and 2621618. The enzymes used in the art are in most cases penicillin acylases obtained from *Escherichia coli* and are immobilized on various types of water-insoluble materials.

A drawback of the known enzymatic methods for the production of amoxycillin, ampicillin, cephadroxil, cephalexin, and cephradine is the high cost due to the selectivity of the immobilized enzyme. Said immobilized enzymes are capable of condensing activated side chain derivatives such as D(-)-phenylglycine amide (PGA), D(-)-phenylglycine methyl ester (PGM), D(-)-4-hydroxyphenylglycine amide (HPGA), D(-)-4-hydroxyphenylglycine methyl ester (HPGM), D(-)-2,5-dihydro-phenylglycine amide (DPGA), and D(-)-2,5-dihydrophenylglycine methyl ester (DPGM) with amino β-lactams such as 6-amino-penicillanic acid (6-APA), 7-aminocephalosporanic acid (7-ACA), 7-amino-3-chloro-3-cephem-4-carboxylic acid (7-ACCA), 7-aminodesacetoxycephalosporanic acid (7-ADCA) and 7-amino-3-[(Z)-1-propenyl]-3-cephem-4-carboxylic acid. On the other hand, said immobilized enzymes will also hydrolyse the activated side chain derivatives to worthless side chain acids. Also, the desired product hydrolyses to form side chain acid and the parent amino β-lactam. A high ratio between synthesis and hydrolysis will lower the cost of activated side chain derivative.

From international patent application Wo 93/12250 it is known that the ratio synthesis/hydrolysis for cephadroxil and cephalexin synthesis by *Escherichia coli* penicillin G acylase immobilized on Eupergit PCA is strongly dependent on the reaction conditions such as pH, concentration of reactants and temperature. The influence of the nature of the carrier material on the ratio synthesis/hydrolysis however, has not been taught.

From European Patent No. 222,462 and corresponding U.S. Pat. No. 5,137,818. It is known that amino groups can be introduced onto the carrier material by adding aminopolymers such as alginate amine, chitosan, pectin, or polyethylene imine to the base gelling constituent of the carrier.

Surprisingly, it has been found that immobilization of *Escherichia coli* penicillin G acylase on a carrier consisting of a gelling agent and a polymer containing free amino groups gives an enzymatic catalyst with superior characteristics regarding the ratio synthesis/hydrolysis in the condensation reaction of activated side chain derivatives with amino β-lactams as compared to penicillin G acylases immobilized on other carriers.

SUMMARY OF THE INVENTION

The present invention provides Penicillin G acylase immobilized on a carrier comprising a gelling agent and a polymer containing free amino groups. Preferably the polymer is selected from the group consisting of alginate amine, chitosan, pectin, or polyethylene imine, and more preferably, the gelling agent is gelatin. Furthermore, by applying such an immobilized enzyme, an improved process for the preparation of a β-lactam derivative by an enzymatic reaction of the parent amino β-lactam with the corresponding acylating agent has been provided for.

SPECIFIC EMBODIMENTS

Examples of β-lactam derivatives that may be produced by the process of this invention are amoxycillin, ampicillin, cephaclor, cephadroxil, cephprozil, cephalexin, and cephradine. The acylase activity is independent of the substituents at the 3-position of the cephem compounds, e.g. hydrogen, halogen, (lower) alkoxy, methyl or methyl substituted with, for instance, (lower) alkoxy, (lower) alkanoyloxy, halogen, S-$R_5$ (where $R_5$ is (lower) alkyl, (lower) alkanoyl or an optionally substituted heterocyclic ring), $N_+$-$R_6$ (where $R_6$ is (lower) alkyl or an optionally substituted heterocyclic ring). By lower is meant 1–6 carbon atoms. A heterocyclic ring is defined as an unsaturated ring structure comprising at least one nitrogen, sulphur or oxygen atom.

The acylating agent may be a derivative of D(-)-phenylglycine, D(-)-4-hydroxyphenylglycine or D(-)-2,5-dihydro-phenylglycine such as a lower alkyl (methyl, ethyl, n-propyl or isopropyl) ester or an amide which is unsubstituted in the —$CONH_2$ group.

The corresponding amino β-lactam contains the same β-lactam nucleus as the β-lactam derivative prepared.

Generally, the reaction temperature of the process of this invention may vary between 0° C. and 35° C. The optimal temperature depends on the substrates as has been mentioned in European patent application 473008 and has not been optimized in the comparative examples given. The suitable pH value depends on the nature and concentration of the substrates and is typically in the range of 5 to 9. For convenient operation control of pH is used. Suitable reaction times are from several minutes to several hours, in particular from 30 minutes to three hours.

In commercial processes involving the use of a catalyst e.g. an enzyme, the price of the catalyst is often an important parameter in the overall economy of the process. In such cases it is an advantage if the catalyst can be reused without loss of catalytic activity. To this end, it is advantageous to have the enzyme in a reusable form, for example, in immobilized or entrapped form. The following immobilized *Escherichia coli* penicillin acylases were investigated:

Type A: *Escherichia coli* penicillin acylase isolated as described in international patent application Wo 92/12782. Immobilization was carried out as described in European Patent No. 222,462 and corresponding U.S. Pat. No. 5,137,818.

Type B: Commercially available immobilized *Escherichia coli* penicillin G acylase from Recordati, Italy, as described in European patent application No. 473008.

Type C: Commercially available immobilized *Escherichia coli* penicillin G acylase from Boehringer Mannheim GmbH, Germany, known as Enzygel®.

Suitable enzyme concentrations may be from 0.1 U.ml$^{-1}$ to 100 U.ml$^{-1}$ (1 U=one unit of enzyme activity, see below). Using the process according to this invention, extraordinary high synthesis/hydrolysis ratio's can be obtained.

DEFINITIONS AND METHODS OF ANALYSIS

Enzyme Activity

As definition of penicillin G acylase activity the following is used: one unit (U) corresponds to the amount of enzyme that hydrolyses per minute 1 μmole penicillin G under standard conditions (100 g.l$^{-1}$ penicillin G potassium salt, 0.05 M potassium phosphate buffer, pH 8.0, 28° C.).

HPLC Analysis

Procedure A (amoxycillin)
Sample: 1:10 Dilution using 25% acetonitrile in 2 mM potassium phosphate buffer, pH 5
Column: Chromsphere C18, 5 μm (100×3.0 mm)
Solvent: 25% acetonitrile in 12 mM potassium phosphate buffer containing 0.2% sodium dodecyl sulphate, pH 2.6
Flow: 1 ml.min$^{-1}$
Detection: 214 nm
Retention: HPG (1.9 min); HPGA (3.1 min); 6-APA (3.4 min); amoxycillin (4.8 min); HPGM (7.3 min)

Procedure B (cephalexin)
Sample: 1:10 Dilution using 25% acetonitrile in 2 mM potassium phosphate buffer, pH 5
Column: Chromsphere C18, 5 μm (100×3.0 mm)
Solvent: 29% acetonitrile in 5 mM potassium phosphate buffer containing 0.2% sodium dodecyl sulphate, pH 3.1
Flow: 1 ml.min$^{-1}$
Detection: 214 nm
Retention: PG (0.8 min); 7-ADCA (1.3 min); PGA (3.7 min); cephalexin (6.2 min); PGM (7.8 min)

Procedure C (cephradine)
Sample: 1:150 Dilution using 3% 1-propanol in 50 mM phosphoric acid buffer, pH 3.0
Column: Nucleosil 120 3 C18 (250×4.0 mm)
Solvent: Eluent A: 50 mM phosphoric acid buffer, pH 3.0
Eluent B: 50% eluent A, 50% acetonitrile Gradient: 0–5 min: 100% A; 5–10 min: from 100% A to 70% A; 10–18 min: 70% A; 18–18.1 min: from 70% A to 100% A.
Flow: 1 mi.min$^{-1}$
Detection: 220 nm
Retention: 7-ADCA (5.3 min); DPG (6.0 min); DPGA (9.1 min); DPGM (15.9 min); cephradine (18.5 min)

Procedure D (cephaclor)
Sample: 1:150 Dilution using 3% 1-propanol in 50 mm phosphoric acid buffer, pH 3.0
Column: Nucleosil 120 3 C18 (250×4.0 mm)
Solvent: Eluent A: 50 mM phosphoric acid buffer, pH 3.0
Eluent B: 50% eluent A, 50% acetonitrile Gradient: 0–5 min: 100% A; 5–10 min: from 100% A to 70% A; 10–18 min: 70% A; 18–18.1 min: from 70% A to 100% A.
Flow: 1 ml.min$^{-1}$
Detection: 220 nm
Retention: 7-ACCA (3.2 min); PG (3.8 min); PGA (5.6 min); cephaclor (14.9 min)

Procedure E (ampicillin)
Sample: 1:200 Dilution using 33% acetonitrile in 3.4 mM potassium phosphate buffer, pH 6.9
Column: Chromsphere C18, 5 μm (100×3.0 mm)
Solvent: 30% Acetonitrile in 5 mM potassium phosphate buffer containing 0.1% sodium dodecyl sulphate, pH 3.0
Flow: 1 ml.min$^{-1}$
Detection: 214 nm
Retention: PG (1.0 min); 6-APA (1.3 min); PGA (2.6 min); ampicillin (4.5 min); PGM (5.8 min)

EXAMPLE 1

Synthesis of Amoxycillin from 6-APA and HPGA Using Immobilized *Escherichia Coli* Penicillin G Acylase To an aqueous solution (50 ml) containing 10 mM HPGA and 30 mM 6-APA is added 50 U of immobilized *Escherichia coli* penicillin G acylase at 21C. The pH is adjusted to 6.0 and the reaction is allowed to proceed under a nitrogen atmosphere with pH control using a 0.05 M solution of H$_2$SO$_4$ in water. At different time intervals (see tables below) samples are analyzed according to procedure A as described above. The molar ratio synthesis/hydrolysis (S/H) is calculated from the results thus obtained.

TABLE 1.1

Synthesis of amoxycillin using type A enzyme

| | Time (min) | | | | | | | | |
|---|---|---|---|---|---|---|---|---|---|
| | 5 | 10 | 15 | 20 | 25 | 30 | 60 | 90 | 120 |
| S/H-ratio | 1.1 | 1.3 | 1.3 | 1.4 | 1.2 | 1.2 | 1.2 | 1.1 | 1.1 |

TABLE 1.2

Synthesis of amoxycillin using type B enzyme

| | Time (min) | | | | | |
|---|---|---|---|---|---|---|
| | 18 | 60 | 90 | 110 | 150 | 180 |
| S/H-ratio | 0.6 | 0.7 | 0.7 | 0.7 | 0.6 | 0.5 |

TABLE 1.3

Synthesis of amoxycillin using type C enzyme

| | Time (min) | | | | |
|---|---|---|---|---|---|
| | 18 | 30 | 60 | 90 | 120 |
| S/H-ratio | 0.7 | 0.7 | 0.6 | 0.6 | 0.5 |

EXAMPLE 2

Synthesis of Anoxycillin from 6-APA and HPXG Using Immobilized *Escherichia Coli* Penicillin G Acylase To an aqueous solution (50 ml) containing 10 mM HPGM and 30 mM 6-APA is added 50 U of immobilized *Escherichia coli* penicillin G acylase at 21° C. The pH is adjusted to 6.0 and the reaction is allowed to proceed under a nitrogen atmosphere with pH control using a 0.05 M solution of H$_2$SO$_4$ in water. At different time intervals (see tables below) samples are analyzed according to procedure A as described above. The molar ratio synthesis/hydrolysis (S/H) is calculated from the results thus obtained.

TABLE 2.1

Synthesis of amoxycillin using type A enzyme

| | Time (min) | | | |
|---|---|---|---|---|
| | 10 | 20 | 40 | 60 |
| S/H-ratio | 1.6 | 1.4 | 1.3 | 1.2 |

EXAMPLE 3

Synthesis of Cephalexin from 7-ADCA and PGA Using Immobilized *Escherichia Coli* Penicillin G Acylase To an aqueous solution (50 ml) containing 10 mM PGA and 30 mM 7-ADCA is added 50 U of immobilized *Escheri-* chia coli penicillin G acylase at 21° C. The pH is adjusted to 7.0 and the reaction is allowed to proceed under a nitrogen atmosphere with pH control using a 0.05 M solution of $H_2SO_4$ in water. At different time intervals (see tables below) samples are analyzed according to procedure B as described above. The molar ratio synthesis/hydrolysis (S/H) is calculated from the results thus obtained.

TABLE 3.1

Synthesis of cephalexin using type A enzyme

| | Time (min) | | | |
|---|---|---|---|---|
| | 5 | 10 | 20 | 30 |
| S/H-ratio | 6.5 | 4.2 | 3.4 | 2.4 |

TABLE 3.2

Synthesis of cephalexin using type B enzyme

| | Time (min) | | | |
|---|---|---|---|---|
| | 5 | 10 | 20 | 30 |
| S/H-ratio | 1.0 | 0.9 | 0.8 | 0.7 |

EXAMPLE 4

Synthesis of Cephradine from 7-ADCA and DPGM.HCl Using Immobilized *Escherichia Coli* Penicillin G Acylase To an aqueous solution (120 ml) containing 300 mM DPGM.HCl and 300 mM 7-ADCA is added immobilized *Escherichia coli* penicillin G acylase (units as given in tables). The pH is adjusted to the value given in the tables below and the reaction is allowed to proceed under a nitrogen atmosphere. At different time intervals samples are analyzed according to procedure C as described above. The molar ratio synthesis/hydrolysis (S/H) is calculated from the results thus obtained.

TABLE 4.1

Synthesis of Cephradine at pH 7.5 using type A enzyme (12 U · ml$^{-1}$)

| | Time (min) | | | | |
|---|---|---|---|---|---|
| | 26 | 62 | 75 | 106 | 120 |
| Conversion (%) | 40 | 63 | 63 | 58 | 54 |
| S/H-ratio | 12 | 4.0 | 2.9 | 2.0 | 1.9 |

TABLE 4.2

Synthesis of Cephradine at pH 7.0 using type B enzyme (33 U · ml$^{-1}$)

| | Time (min) | | | |
|---|---|---|---|---|
| | 45 | 110 | 170 | 255 |
| Conversion (%) | 33 | 49 | 51 | 68 |
| S/H-ratio | 2.4 | 1.7 | 1.4 | 1.4 |

EXAMPLE 5

Synthesis of Cephaclor from 7-ACCA and PGA Using Immobilized *Escherichia Coli* Penicillin G Acylase To an aqueous solution (120 ml) containing PGA and 7-ACCA (concentrations and enzyme units as given in tables below) is added immobilized *Escherichia coli* penicillin G acylase. The pH is adjusted to 7.7 and the reaction proceeds with pH control using a 2.0 M solution of $H_2SO_4$ in water. At different time intervals (see tables below) samples are analyzed according to procedure D as described above. The molar ratio synthesis/hydrolysis (S/H) is calculated from the results thus obtained.

TABLE 5.1

Synthesis of cephaclor from PGA (0.5 M) and 7-ACCA (0.6 M) using type A enzyme (9 U · ml$^{-1}$)

| | Time (min) | | |
|---|---|---|---|
| | 2 | 62 | 90 |
| Conversion (%) | 3 | 58 | 66 |
| S/H-ratio | 2.0 | 6.2 | 4.0 |

TABLE 5.2

Synthesis of cephaclor from PGA (0.6 M) and 7-ACCA (0.6 M) using type B enzyme (47 U · ml$^{-1}$)

| | Time (min) | | | | |
|---|---|---|---|---|---|
| | 26 | 62 | 124 | 161 | 266 |
| Conversion (%) | 25 | 40 | 50 | 55 | 58 |
| S/H-ratio | 5.3 | 4.4 | 3.4 | 3.2 | 2.6 |

EXAMPLE 6

Synthesis of Ampicillin from 6-APA and PGA Using Immobilized *Escherichia Coli* Penicillin G Acylase To an aqueous solution (100 ml) containing 500 mM PGA and 300 mM 6-APA is added 100 U of immobilized *Escherichia coli* penicillin G acylase. The pH is adjusted to 7.5 and the reaction is allowed to proceed with pH control using a 6.0 M solution of HCl in water. At different time intervals samples are analyzed according to procedure E as described above. The conversion and the molar ratio synthesis/hydrolysis (S/H) are calculated from the results thus obtained and given in the tables below.

TABLE 6.1.1

Synthesis of Ampicillin using type A enzyme (as polymer alginate amine has been used)

| | Alginate amine (%) | | | | | |
|---|---|---|---|---|---|---|
| | 0 | | 1.0 | 2.0 | | 3.0 |
| Conversion (%) | 5 | 5 | 10 | 5 | 5 | 10 |
| Time (min) | 115 | 54 | 116 | 151 | 68 | 135 |
| S/H-ratio | 2.4 | 4.6 | 3.5 | 3.9 | 3.9 | 2.9 |

TABLE 6.1.2

Synthesis of Ampicillin using type A enzyme
(as polymer chitosan amine has been used)

| | Chitosan (%) | | | | | | | | | |
|---|---|---|---|---|---|---|---|---|---|---|
| | 0 | 1.0 | | 1.5 | | 2.0 | | 2.5 | | 3.0 |
| Conversion (%) | 5 | 5 | 10 | 5 | 10 | 5 | 10 | 5 | 10 | 5 | 10 |
| Time (min) | 115 | 34 | 73 | 22 | 51 | 26 | 62 | 30 | 57 | 26 | 52 |
| S/H-ratio | 2.4 | 2.5 | 2.6 | 2.4 | 2.4 | 2.1 | 2.1 | 2.5 | 2.0 | 3.4 | 3.4 |

TABLE 6.1.3

Synthesis of Ampicillin using type A enzyme
(as polymer pectin has been used)

| | Pectin (%) | | | | |
|---|---|---|---|---|---|
| | 0 | 2.0 | | 3.0 | |
| Conversion (%) | 5 | 5 | 10 | 5 | 10 |
| Time (min) | 115 | 65 | 133 | 45 | 94 |
| S/H-ratio | 2.4 | 2.4 | 1.9 | 3.5 | 2.7 |

TABLE 6.1.4

Synthesis of Ampicillin using type A enzyme
(as polymer polyethylene imine has been used)

| | Polyethylene imine (%) | | | | | | |
|---|---|---|---|---|---|---|---|
| | 0 | 1.0 | | 2.0 | | 3.0 | |
| Conversion (%) | 5 | 5 | 10 | 5 | 10 | 5 | 10 |
| Time (min) | 115 | 64 | 132 | 49 | 100 | 43 | 93 |
| S/H-ratio | 2.4 | 2.5 | 2.4 | 2.4 | 2.8 | 2.7 | 2.5 |

TABLE 6.2

Synthesis of Ampicillin using type B enzyme

| | Conversion (%) | |
|---|---|---|
| | 5 | 10 |
| Time (min) | 43 | 92 |
| S/H-ratio | 2.3 | 2.4 |

TABLE 6.3

Synthesis of Ampicillin using type C enzyme

| | Conversion (%) | |
|---|---|---|
| | 5 | 10 |
| Time (min) | 33 | 69 |
| S/H-ratio | 3.3 | 2.8 |

What is claimed is:

1. Penicillin G acylase immobilized by covalent bonding to a carrier comprising a crosslinked mixture of gelled gelatin and a polymer containing free amino groups.

2. Penicillin G acylase according to claim 1, wherein the penicillin G acylase is from *Escherichia coli, Actetobacter pasteurianum, Xanthomonas citrii, kluyvera citrophila, Bacillus megaterium* or *Alcaligenes faecalis*.

3. A process for the preparation of a β-lactam derivative comprising reacting an amino β-lactam with an acylating agent in the presence of the immobilized Penicillin G acylase, as defined in claim 1.

4. The process according to claim 3, wherein the acylating agent is selected from the group consisting of a derivative of D-phenylglycine, a derivative of D-p-hydroxyphenylglycine, and a derivative of D-2,5-dihydrophenylglycine.

5. The process according to claim 3, wherein the β-lactam derivative is selected from the group consisting of ampicillin, amoxycillin, cephaclor, cephalexin, cephadroxil, cephradine and cephprozil.

6. The process according to claim 3, wherein reacting is performed at a temperature in the range from about 0 to about 35° C.

7. The process according to claim 3, wherein reacting is performed at a pH value in the range from above about 5 through about 9.

8. The process of claim 6 wherein the temperature is above about 10° C.

* * * * *